US008968193B2

(12) United States Patent
Li et al.

(10) Patent No.: US 8,968,193 B2
(45) Date of Patent: Mar. 3, 2015

(54) SYSTEM AND METHOD FOR ENABLING A RESEARCH MODE ON PHYSIOLOGICAL MONITORS

(75) Inventors: Li Li, Milpitas, CA (US); Scott Amundson, Oakland, CA (US); James Ochs, Seattle, WA (US)

(73) Assignee: Covidien LP, Mansfield, MA (US)

( * ) Notice: Subject to any disclaimer, the term of this patent is extended or adjusted under 35 U.S.C. 154(b) by 1507 days.

(21) Appl. No.: 12/241,300

(22) Filed: Sep. 30, 2008

(65) Prior Publication Data

US 2010/0081890 A1    Apr. 1, 2010

(51) Int. Cl.
*A61B 5/00*  (2006.01)
*A61B 5/1455*  (2006.01)
*G06F 19/00*  (2011.01)

(52) U.S. Cl.
CPC .............. *A61B 5/14551* (2013.01); *A61B 5/72* (2013.01); *A61B 5/7235* (2013.01); *A61B 5/7271* (2013.01); *G06F 19/3431* (2013.01); *G06F 19/3437* (2013.01); *G06F 19/3406* (2013.01); *A61B 5/7475* (2013.01); *Y10S 128/923* (2013.01)
USPC ........... 600/300; 600/323; 600/324; 600/502; 600/301; 128/923; 705/2; 705/3

(58) Field of Classification Search
CPC ........................ A61B 5/02; A61B 5/72; A61B 5/7271–5/7278; A61B 5/7235–5/725; A61B 5/02416; A61B 5/14551; G06F 19/3406; G06F 19/3431; G06F 19/3437
USPC .................. 600/300, 301; 128/903–905, 920; 705/2–5
See application file for complete search history.

(56) References Cited

U.S. PATENT DOCUMENTS

| | | | |
|---|---|---|---|
| 3,638,640 | A | 2/1972 | Shaw |
| 4,714,341 | A | 12/1987 | Hamaguri et al. |
| 4,805,623 | A | 2/1989 | Jöbsis |
| 4,807,631 | A | 2/1989 | Hersh et al. |
| 4,911,167 | A | 3/1990 | Corenman et al. |

(Continued)

FOREIGN PATENT DOCUMENTS

| | | |
|---|---|---|
| CA | 2179022 | 6/1995 |
| DE | 4210102 | 9/1993 |

(Continued)

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

(Continued)

*Primary Examiner* — William Thomson
*Assistant Examiner* — Marie Archer
(74) *Attorney, Agent, or Firm* — Fletcher Yoder PC

(57) ABSTRACT

The present disclosure may provide a system and method for analyzing data acquired using a physiological monitor. In one embodiment, the analysis is performed on the physiological monitor and results in the analysis of data collected by the physiological monitor over an interval of time. The analysis may include comparing the data to sample data representative of known disease states and/or may include performing statistical analyses or recalculations of the data based on adjusted monitor settings. In one embodiment, the settings of the physiological monitor may be adjusted based on the results of the analyses.

21 Claims, 4 Drawing Sheets

(56) References Cited

U.S. PATENT DOCUMENTS

| | | | |
|---|---|---|---|
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,299,118 A * | 3/1994 | Martens et al. | 600/509 |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,398,680 A | 3/1995 | Polson et al. | |
| 5,413,099 A | 5/1995 | Schmidt et al. | |
| 5,448,991 A | 9/1995 | Polson et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,499,627 A | 3/1996 | Steuer et al. | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,626,140 A | 5/1997 | Feldman et al. | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Kuenstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,803,908 A | 9/1998 | Steuer et al. | |
| 5,820,550 A | 10/1998 | Polson et al. | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,934,277 A | 8/1999 | Mortz | |
| 5,978,691 A | 11/1999 | Mills | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,385,471 B1 | 5/2002 | Mortz | |
| 6,397,091 B2 | 5/2002 | Diab et al. | |
| 6,398,727 B1 * | 6/2002 | Bui et al. | 600/300 |
| 6,415,166 B1 | 7/2002 | Van Hoy et al. | |
| 6,415,236 B2 | 7/2002 | Kobayashi et al. | |
| 6,419,671 B1 | 7/2002 | Lemberg | |
| 6,425,861 B1 * | 7/2002 | Haberland et al. | 600/300 |
| 6,438,399 B1 | 8/2002 | Kurth | |
| 6,461,305 B1 | 10/2002 | Schnall | |
| 6,463,320 B1 * | 10/2002 | Xue et al. | 600/523 |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,527,725 B1 | 3/2003 | Inukai et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,681,128 B2 | 1/2004 | Steuer et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,714,803 B1 | 3/2004 | Mortz | |
| 6,731,274 B2 | 5/2004 | Powell | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,839,581 B1 | 1/2005 | El-Solh et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,896,661 B2 | 5/2005 | Dekker et al. | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,987,994 B1 | 1/2006 | Mortz | |
| 6,993,371 B2 | 1/2006 | Kiani et al. | |
| 6,996,427 B2 | 2/2006 | Ali et al. | |
| 6,997,880 B2 | 2/2006 | Carlebach et al. | |
| 7,001,334 B2 | 2/2006 | Reed et al. | |
| 7,001,337 B2 | 2/2006 | Dekker et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,127,278 B2 | 10/2006 | Melker et al. | |
| 7,162,306 B2 | 1/2007 | Caby et al. | |
| 7,181,264 B2 | 2/2007 | Wiesmann et al. | |

(56) References Cited

U.S. PATENT DOCUMENTS

| | | |
|---|---|---|
| 7,209,775 B2 | 4/2007 | Bae et al. |
| 7,236,811 B2 | 6/2007 | Schmitt |
| 7,263,395 B2 | 8/2007 | Chan et al. |
| 7,272,426 B2 | 9/2007 | Schmid |
| 7,277,752 B2 | 10/2007 | Matos |
| 7,309,314 B2 | 12/2007 | Grant et al. |
| 7,317,939 B2 | 1/2008 | Fine et al. |
| 7,353,054 B2 | 4/2008 | Kawasaki et al. |
| 7,366,569 B2 | 4/2008 | Belalcazar |
| 7,373,193 B2 | 5/2008 | Al-Ali et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0019584 A1* | 2/2002 | Schulze et al. ............... 600/300 |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0023178 A1 | 1/2003 | Bischoff et al. |
| 2003/0055324 A1 | 3/2003 | Wasserman |
| 2003/0060693 A1 | 3/2003 | Monfre et al. |
| 2003/0117296 A1* | 6/2003 | Seely ....................... 340/870.07 |
| 2003/0139687 A1 | 7/2003 | Abreu |
| 2003/0144584 A1 | 7/2003 | Mendelson |
| 2003/0158466 A1 | 8/2003 | Lynn et al. |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0039742 A1 | 2/2005 | Hickle |
| 2005/0070774 A1 | 3/2005 | Addison et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0224058 A1 | 10/2006 | Mannheimer |
| 2006/0229519 A1 | 10/2006 | Fujiwara et al. |
| 2006/0247501 A1 | 11/2006 | Ali |
| 2006/0258921 A1 | 11/2006 | Addison et al. |
| 2006/0276695 A9 | 12/2006 | Lynn et al. |
| 2006/0287590 A1 | 12/2006 | Mceowen |
| 2007/0032732 A1 | 2/2007 | Shelley et al. |
| 2007/0062531 A1 | 3/2007 | Fisher et al. |
| 2007/0093721 A1 | 4/2007 | Lynn et al. |
| 2007/0118028 A1 | 5/2007 | Kitajima et al. |
| 2007/0142719 A1 | 6/2007 | Kawasaki et al. |
| 2007/0149860 A1 | 6/2007 | Lynn et al. |
| 2007/0149870 A1 | 6/2007 | Rosenthal |
| 2007/0149890 A1 | 6/2007 | Li et al. |
| 2007/0167851 A1 | 7/2007 | Vitali et al. |
| 2007/0179386 A1 | 8/2007 | Michard et al. |
| 2007/0219059 A1 | 9/2007 | Schwartz et al. |
| 2008/0045809 A1 | 2/2008 | Hermannsson |
| 2008/0064965 A1 | 3/2008 | Jay et al. |
| 2008/0076992 A1 | 3/2008 | Hete et al. |
| 2008/0091092 A1 | 4/2008 | Al-Ali |
| 2008/0132770 A1 | 6/2008 | Ayers et al. |
| 2008/0154098 A1 | 6/2008 | Morris et al. |
| 2008/0188729 A1 | 8/2008 | Sato et al. |
| 2008/0208912 A1 | 8/2008 | Garibaldi |
| 2008/0221401 A1* | 9/2008 | Derchak et al. ............... 600/301 |
| 2008/0255432 A1* | 10/2008 | Nielsen et al. ............... 600/301 |

FOREIGN PATENT DOCUMENTS

| | | |
|---|---|---|
| EP | 0615723 | 9/1994 |
| EP | 0630203 | 12/1994 |
| EP | 1491135 | 12/2004 |
| JP | 63275325 | 11/1988 |
| JP | 2237544 | 9/1990 |
| JP | 3170866 | 7/1991 |
| JP | 4332536 | 11/1992 |
| JP | 7124138 | 5/1995 |
| JP | 3238813 | 7/1995 |
| JP | 8256996 | 10/1996 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| JP | 2005034472 | 2/2005 |
| JP | 25095465 | 4/2005 |
| JP | 27117591 | 5/2007 |
| JP | 27167185 | 7/2007 |
| JP | 28119026 | 5/2008 |
| WO | WO9309711 | 5/1993 |
| WO | WO9423643 | 10/1994 |
| WO | WO9639927 | 12/1996 |
| WO | WO9843071 | 10/1998 |
| WO | WO9932030 | 7/1999 |
| WO | WO0021438 | 4/2000 |
| WO | WO0140776 | 6/2001 |
| WO | WO0176461 | 10/2001 |
| WO | WO0176471 | 10/2001 |
| WO | WO03000125 | 1/2003 |
| WO | WO03039326 | 5/2003 |
| WO | WO03096893 | 11/2003 |
| WO | WO2004075746 | 9/2004 |
| WO | WO2005064314 | 7/2005 |
| WO | WO2006067725 | 6/2006 |
| WO | WO2006109072 | 10/2006 |
| WO | WO2007131064 | 11/2007 |
| WO | WO2007131066 | 11/2007 |
| WO | WO2007141121 | 12/2007 |
| WO | WO2008075288 | 6/2008 |

OTHER PUBLICATIONS

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

(56) References Cited

OTHER PUBLICATIONS

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engin.*

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Kaestle, S.; "Determining Artefact Sensitivity of New Pulse Oximeters in Laboratory Using Signals Obtained from Patient," *Biomedizinische Technik*, vol. 45 (2000).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.,"Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spiguilis, Janis, et al.; "Optical multi-channel sensing of skin blood pulsations," *Optical Sensing, Proceedings of SPIE*, vol. 5459, pp. 46-53 (2004).

Cysewska-Sobusaik, Anna; "Metrological Problems With noninvasive Transillumination of Living Tissues," *Proceedings of SPIE*, vol. 4515, pp. 15-24 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

\* cited by examiner

# SYSTEM AND METHOD FOR ENABLING A RESEARCH MODE ON PHYSIOLOGICAL MONITORS

BACKGROUND

The present disclosure relates generally to medical devices, and, more particularly, to a physiological monitor having research capabilities.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a perennial feature of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood, the volume of individual blood pulsations supplying the tissue, and/or the rate of blood pulsations corresponding to each heartbeat of a patient.

In practice, a pulse oximeter may be employed to provide a running assessment of a patient's physiological signs, such as pulse rate and blood oxygen saturation, and to indicate when one ort more of the monitored characteristics crosses an alarm or threshold value. However, in addition to this monitoring function, a pulse oximeter may also store the measured physiological data as it is collected over time. A pulse oximeter may allow some limited functionality in reviewing the measured data, such as displaying a historical trendline or waveform representing a measured physiological characteristic, but such review capabilities typically do not provide for meaningful analysis of the collected data. Instead, to the extent the collected physiological data is to be analyzed, the data may be exported to an external device, such as a computer or workstation, for analysis. The process of exporting data, however, may be complicated and/or time consuming and may remove the pulse oximeter from its principal monitoring duties. Further, the analysis of the collected data may utilize equipment and/or tools that are costly and/or not readily available.

SUMMARY

Certain aspects commensurate in scope with the original claims are set forth below. It should be understood that these aspects are presented merely to provide the reader with a brief summary of certain embodiments and that these aspects are not intended to limit the scope of the claims. Indeed, the claims and disclosure may encompass a variety of aspects that may not be set forth below.

A method for analyzing data is provided in an embodiment. In accordance with this embodiment, data is collected over a time interval using a physiological monitor. The data is analyzed on the physiological monitor.

In accordance with an embodiment, a method for analyzing data is provided. In accordance with this embodiment, a research mode on a physiological monitor is entered in response to a user input. A set of data acquired by the physiological monitor over a time interval is accessed and one or more analyses are executed to analyze the set of data. The results of the one or more analysis routines are displayed.

In accordance with an embodiment, a physiological monitor is provided. The physiological monitor includes a port capable of receiving sensor data and one or more memory or storage devices capable of at least storing the sensor data, one or more derived physiological characteristics, and/or one or more analysis routines. The physiological monitor also includes one or more processors capable of processing the sensor data to derive the one or more physiological characteristics and of executing the one or more analysis routines to analyze at least the sensor data or the physiological characteristics.

In an embodiment, a system is provided. The system includes a physiological monitor capable of analyzing data when placed in a research mode. The system also includes one or more electronic devices in communication with the physiological monitor. The one or more electronic devices are capable of placing the physiological monitor in the research mode and/or of viewing the results of the research mode

BRIEF DESCRIPTION OF THE DRAWINGS

Advantages of the disclosure may become apparent upon reading the following detailed description and upon reference to the drawings in which.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Physiological monitors, such as pulse oximeters may be employed to provide running measurements of a patient's physiological characteristics and to alert caregivers when such measurements are abnormal. However, the physiological data collected over time by such devices may also provide useful information, such as diagnostic information, about a patient. For example, the analysis of hours or days worth of pulse oximetry data may provide useful information about a patient's susceptibility to apnea events or other respiratory or circulatory disorders. Further such analyses and/or diagnoses may suggest more appropriate monitoring parameters for the patient when using the physiological monitor, such as a pulse oximeter. However, it may be difficult or inconvenient to download the collected physiological data to an appropriate analysis platform, such as a computer. Accordingly, it may be desirable to provide analysis functionality on the monitor, such as on a pulse oximeter.

Figure 1:
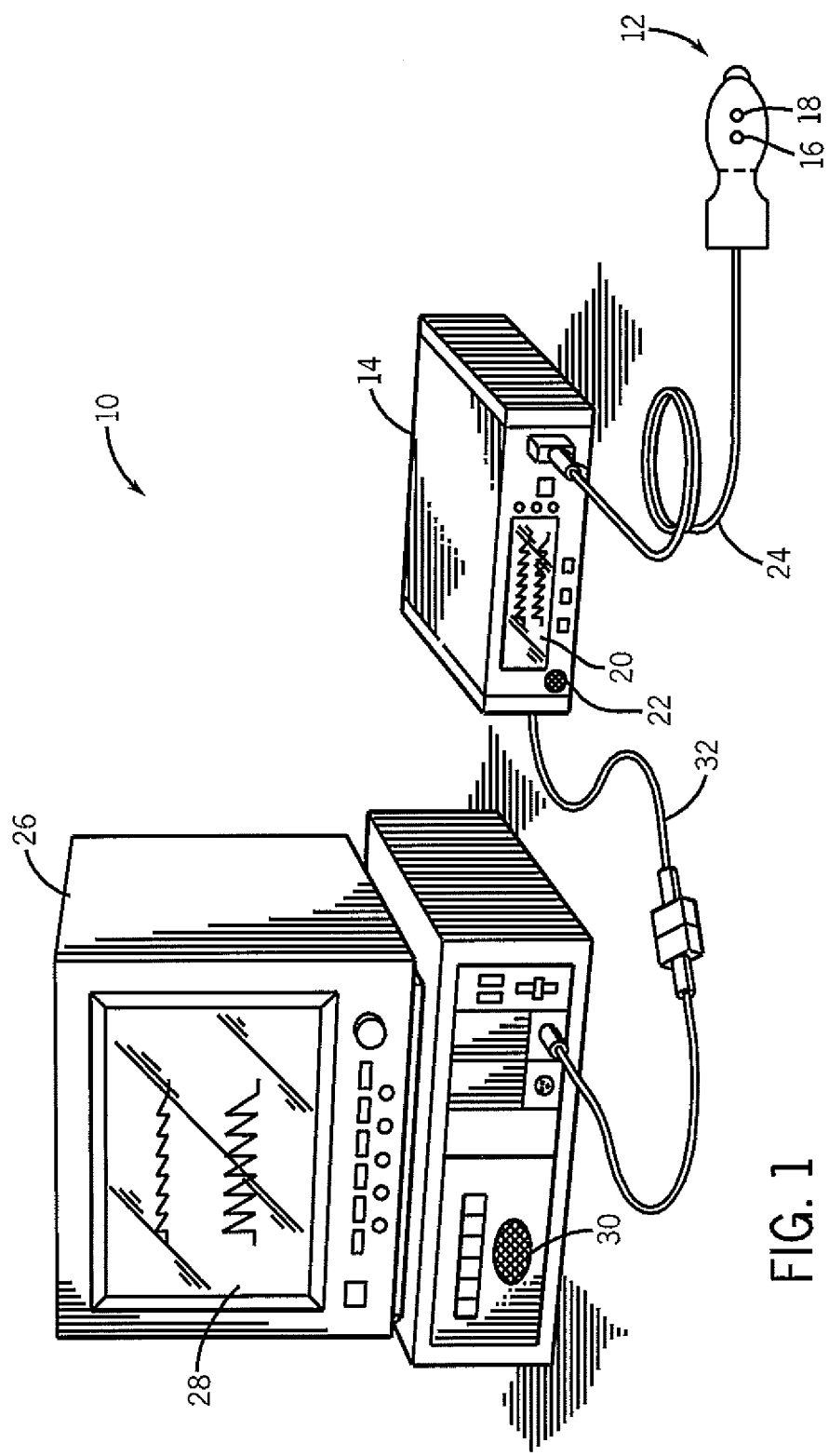
FIG. 1 is a perspective view of a pulse oximeter coupled to a multi-parameter patient monitor and a sensor in accordance with embodiments.

FIG. 1 is a perspective view of such a pulse oximetry system 10 in accordance with an embodiment. The system 10 includes a sensor 12 and a pulse oximetry monitor 14. The sensor 12 includes an emitter 16 for emitting light at certain wavelengths into a patient's tissue and a detector 18 for detecting the light after it is reflected and/or absorbed by the patient's tissue. The monitor 14 may be capable of calculating physiological characteristics received from the sensor 12 relating to light emission and detection. Further, the monitor 14 includes a display 20 capable of displaying the physiological characteristics, other information about the system, and/or alarm indications. The monitor 14 also includes a speaker 22 to provide an audible alarm in the event that the patient's physiological characteristics exceed a threshold. The sensor 12 may be communicatively coupled to the monitor 14 via a cable 24. However, in other embodiments a wireless transmission device or the like may be utilized instead of or in addition to the cable 24.

In the illustrated embodiment, the pulse oximetry system 10 also includes a multi-parameter patient monitor 26. In addition to the monitor 14, or alternatively, the multi-parameter patient monitor 26 may be capable of calculating physiological characteristics and providing a central display 28 for information from the monitor 14 and from other medical monitoring devices or systems. For example, the multi-parameter patient monitor 26 may display a patient's $SpO_2$ and pulse rate information from the monitor 14 and blood pressure from a blood pressure monitor on the display 28. Additionally, the multi-parameter patient monitor 26 may indicate an alarm condition via the display 28 and/or a speaker 30 if the patient's physiological characteristics are found to be outside of the normal range. The monitor 14 may be communicatively coupled to the multi-parameter patient monitor 26 via a cable 32 coupled to a sensor input port or a digital communications port. In addition, the monitor 14 and/or the multi-parameter patient monitor 26 may be connected to a network to enable the sharing of information with servers or other workstations.

Figure 2:
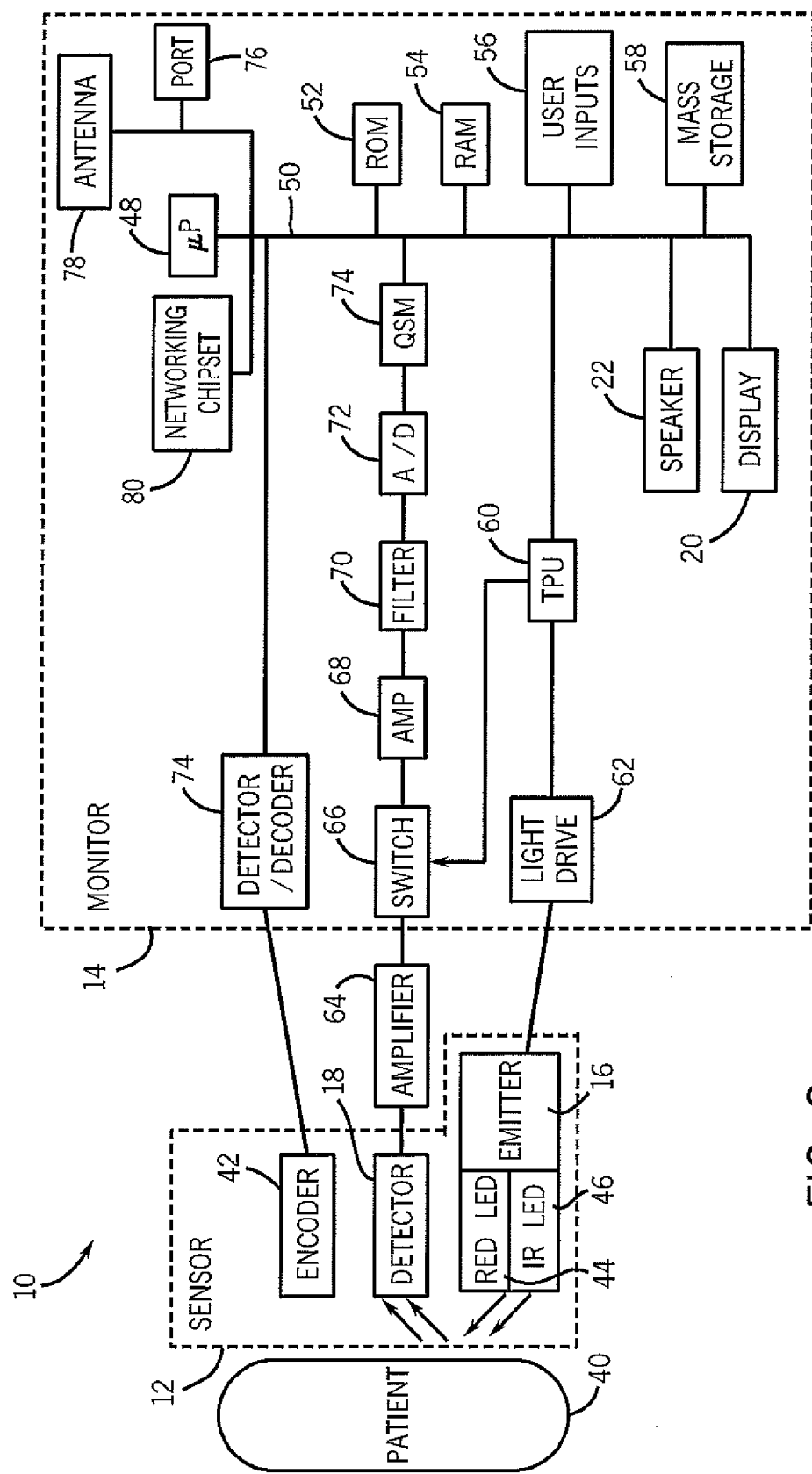
FIG. 2 is a block diagram of the pulse oximeter and sensor coupled to a patient in accordance with embodiments.

FIG. 2 is a block diagram of the exemplary pulse oximetry system 10 of FIG. 1 coupled to a patient 40 in accordance with embodiments. Examples of pulse oximeters that may be used in the implementation of the present disclosure include pulse oximeters available from Nellcor Puritan Bennett LLC, but the following discussion may be applied to other pulse oximeters and medical devices. Specifically, certain components of the sensor 12 and the monitor 14 are illustrated in FIG. 2. The sensor 12 may include the emitter 16, the detector 18, and an encoder 42. It should be noted that the emitter 16 may be capable of emitting at least two wavelengths of light e.g., RED and IR, into a patient's tissue 40. Hence, the emitter 16 may include a RED LED 44 and an IR LED 46 for emitting light into the patient's tissue 40 at the wavelengths used to calculate the patient's physiological characteristics. In certain embodiments, the RED wavelength may be between about 600 nm and about 700 nm, and the IR wavelength may be between about 800 nm and about 1000 nm. Alternative light sources may be used in other embodiments. For example, a single wide-spectrum light source may be used, and the detector 18 may be capable of detecting certain wavelengths of light. In another example, the detector 18 may detect a wide spectrum of wavelengths of light, and the monitor 14 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In an embodiment, the detector 18 may be capable of detecting the intensity of light at the RED and IR wavelengths. In operation, light enters the detector 18 after passing through the patient's tissue 40. The detector 18 may convert the intensity of the received light into an electrical signal. The light intensity may be directly related to the absorbance and/or reflectance of light in the tissue 40. That is, when more light at a certain wavelength is absorbed or reflected, less light of that wavelength is typically received from the tissue by the detector 18. After converting the received light to an electrical signal, the detector 18 may send the signal to the monitor 14, where physiological characteristics may be calculated based at least in part oil the absorption of the RED and IR wavelengths in the patient's tissue 40.

The encoder 42 may contain information about the sensor 12, such as what type of sensor it is (e.g., whether the sensor is intended for placement on a forehead or digit) and the wavelengths of light emitted by the emitter 16. This information may allow the monitor 14 to select appropriate algorithms and/or calibration coefficients for calculating the patient's physiological characteristics. The encoder 42 may, for instance, be a coded resistor which stores values corresponding to the type of the sensor 12 and/or the wavelengths of light emitted by the emitter 16.

These coded values may be communicated to the monitor 14, which determines how to calculate the patient's physiological characteristics. In another embodiment, the encoder 42 may be a memory on which one or more of the following information may be stored for communication to the monitor 14: the type of the sensor 12; the wavelengths of light emitted by the emitter 16; and the proper calibration coefficients and/or algorithms to be used for calculating the patient's physiological characteristics. Pulse oximetry sensors capable of cooperating with pulse oximetry monitors include the OxiMax® sensors available from Nelicor Puritan Bennett LLC.

In an embodiment, signals from the detector 18 and the encoder 42 may be transmitted to the monitor 14. The monitor 14 generally may include processors 48 connected to an internal bus 50. Also connected to the bus may be a read-only memory (ROM) 52, a random access memory (RAM) 54, user inputs 56, one or more mass storage devices 58 (such as hard drives, disk drives, or other magnetic, optical, and/or solid state storage devices), the display 20, or the speaker 22. A time processing unit (TPU) 60 may provide timing control signals to a light drive circuitry 62 which controls when the emitter 16 is illuminated and the multiplexed timing for the RED LED 44 and the IR LED 46. The TPU 60 control the gating-in of signals from detector 18 through an amplifier 64 and a switching circuit 66. These signals may be sampled at the proper time, depending upon which light source is illuminated.

The received signal from the detector 18 may be passed through an amplifier 68, a low pass filter 70, and an analogto-digital converter 72. The digital data may then be stored in a queued serial module (QSM) 74 for later downloading to the RAM 54 or mass storage 58 as the QSM 74 fills up. In one embodiment, there may be multiple separate parallel paths having the amplifier 68, the filter 70, and the JD converter 72 for multiple light wavelengths or spectra received.

The processor(s) 48 may determine the patient's physiological characteristics, such as $SpO_2$ and pulse rate, using various algorithms and/or look-up tables based generally on the value of the received signals corresponding to the light received by the detector 18. In certain embodiments, the processor(s) 48 may also analyze previously acquired physiological characteristics, such as the trend data, to provide diagnoses based upon the trend data and/or to recommend monitor settings for the patient based upon the trend data. For example, the processor(s) 48 may execute analysis routines stored in the ROM 52 and/or the mass storage 58 to analyze trend or other historical data stored in the RAM 54 or mass storage 58.

Signals corresponding to information about the sensor 12 may be transmitted from the encoder 42 to a decoder 74. The decoder 74 may translate these signals to enable the microprocessor to determine the proper method for calculating the patient's physiological characteristics, for example, based generally on algorithms or look-up tables stored in the ROM 52 or mass storage 58. In addition, or alternatively, the encoder 42 may contain the algorithms or look-up tables for calculating the patient's physiological characteristics.

In an embodiment, the monitor 14 may also include one or more mechanisms to facilitate communication with other devices in a network environment. For example, the monitor 14 may include a network port 76 (such as an Ethernet port) and/or an antenna 78 by which signals may be exchanged between the monitor 14 and other devices on a network, such as servers, routers, workstations and so forth. In some embodiments, such network functionality may be facilitated by the inclusion of a networking chipset 80 within the monitor 14, though in other embodiments the network functionality may instead be provided by the processor(s) 48.

Figure 3:
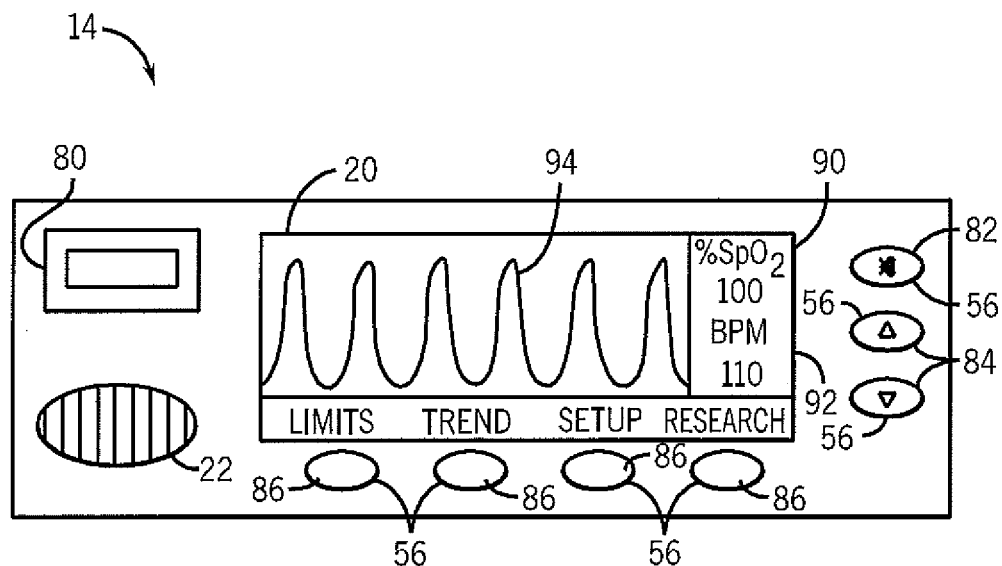
FIGS. 3-4 are exemplary graphical user interfaces of the pulse oximeter in accordance with embodiments.
Figure 4:
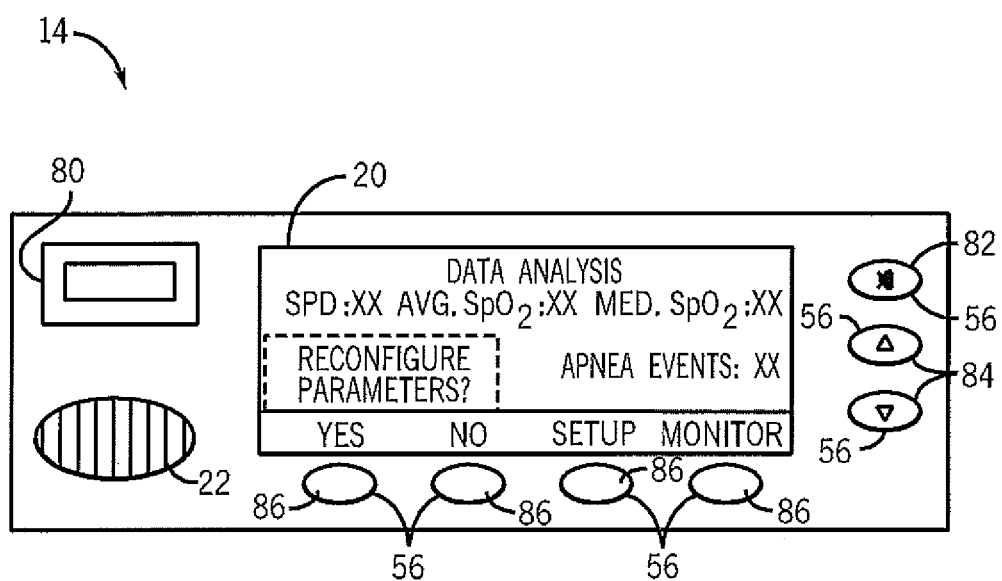

FIGS. 3-4 illustrate an embodiment of a monitor 14 for use in the system 10 (FIG. 1). The monitor 14 may generally include the display 20, the speaker 22, the user inputs 56, and a communication port 80 for coupling the sensor 12 to the monitor 14. In one embodiment, the display 20 may be a standard LCD or CRT type display (such as a VGA or SVGA screen) and the user inputs 56 may be mechanical or electrical buttons, dials, keys, switches and so forth. In other embodiments, the display 20 may be a touchscreen (such as a color or gray-scale screen) and some or all of the user inputs 56 may be locations on the touchscreen corresponding to the desired command or action.

The user inputs 56 may enable the caregiver to control the monitor 14 and change settings. For example, an alarm silence button 82 may enable the caregiver to silence an audible alarm (e.g., when the patient is being cared for), and volume buttons 84 may enable the caregiver to adjust the volume of the alarm and/or any other indicators emitted from the speaker 22. In addition, soft keys 86 may correspond to variable functions, as displayed on the display 22. The soft keys 86 may provide access to further data and/or setting displays. Soft keys 86 provided on the display 20 may enable the caregiver to see and/or change alarm thresholds, view different trend data, change characteristics of the display 20, turn a backlight on or off, or perform other functions.

The monitor 14 may display physiological characteristics, such as, for example, an $SpO_2$ value 90 (i.e., percentage), a pulse rate 92 (i.e., beats per minute), and/or a plethysmographic waveform (i.e., a plot 94) when used to monitor a patient. In the course of such a monitoring operation, the monitor 14 may store the measured physiological data. For example, hours, days, or weeks worth of measured data may be stored on the monitor 14.

In an embodiment, the monitor 14 may include an option to enter a research mode, such as by activating a programmable soft key 86. Such a research mode may allow analysis of some or all of the stored physiological data. For example, selecting the soft key 86 labeled "Research" in FIG. 3 may cause the display of a research mode screen that provides selectable analysis options and/or displays the results (FIG. 4) of such an analysis.

In an embodiment, the monitor 14 may indicate, such as by vistal or audible signals, when the monitor 14 is in research mode as opposed to monitoring mode. For example, as depicted in FIG. 4, the monitor 14 may display a banner or caption (such as "DATA ANALYIS" or "RESEARCH MODE") on the display 20 to indicate when the monitor 14 is in research mode. In this way, a user can be visually and/or audibly alerted that the monitor 14 is displaying data analysis options or results and not the patient's current physiological characteristics. In one embodiment, though the monitor 14 may be in research mode and may not be displaying current measured physiological characteristics, the monitor 14 may still be actively monitoring the patient. Similarly, in some embodiments, the monitor 14 may still display some current measured physiological characteristics even when in research mode, such as in a side bar or along the top or bottom edge of the display 20.

The research mode may allow a user to implement a variety of post-processing analyses of the acquired data over some preceding time frame or may automatically implement one or more of such analyses. For example, in one embodiment, the research mode may automatically or upon user instruction analyze 1, 2, 4, 6, 8, 10, 12, 24, 36, and/or 48 hours of acquired physiological data for a patient (or, indeed, any duration of acquired physiological data sufficient to perform the selected analysis). The analyzed data may or may not be the most recent acquired data. For example, in one embodiment, the analyzed data may not be the most recent data but may instead correspond to a certain period of prior patient activity (such as a sleep cycle or period of exercise). In this manner, irregularities in the physiological characteristic(s) being analyzed may be determined during periods of interest, such as when the patient sleeps or is under physical stress.

In an embodiment, the analyses may take a variety of forms and may include statistical analyses, filtering operations, neural networks, and/or pattern recognition operations. In such an embodiment, the analyses may be performed on the derived physiological characteristics, such as $SpO_2$ and pulse rate, or on the underlying sensed data, i.e., the measurements of light reflectance or transmission at different wavelengths and/or times.

In an embodiment, a monitor 14 may be a pulse oximeter utilized in a sleep lab to evaluate a patient for apnea events or other respiratory irregularities during a sleep cycle. In such an embodiment, after a sleep session the monitor 14 may be placed in research mode, such as by activating the appropriate soft key 86 or location on a touchscreen. In research mode, the physiological data corresponding to the sleep cycle, such as an 8 hour set of $SpO_2$ and/or pulse measurements acquired while the patient slept, may be statistically analyzed to identify patterns in the trend data corresponding to apnea events, to count the number of apnea events, to determine average and/or median $SpO_2$ and/or pulse rate, and/or to calculate an index value (such as a saturation pattern detection (SPD)

index value) categorizing or diagnosing the patient based on the observed data. Such analyses may be specified and/or initiated by a user or may be performed automatically upon entering research mode.

For example, FIG. 4 depicts an embodiment in which a monitor 14 in a data analysis or research mode displays various results of statistical analyses performed on physiological trend data acquired over time. Such results may include an SPD and/or pattern index, average and median $SpO_2$ values, and/or a count of apnea events, as depicted. In addition, as depicted in FIG. 4, a soft key 86 may be programmed and appropriately labeled to return the monitor 14 to a monitor mode. In certain embodiments a time out feature may also be provided so that an interval of time, such as five minutes, with no activity automatically returns the monitor 14 to monitor mode from research mode. In other embodiments, security mechanisms such as a password, barcode, and/or RFID tag may be used to enable research mode.

In an embodiment, the analyses available in the research mode may include manipulating how physiological characteristics were derived and/or sensed data measured over a preceding time interval. For example, for a previously acquired set of measurements, one or more different calibration coefficients may be applied and/or one or more different algorithms for deriving $SpO_2$ or some other characteristic may be applied to the sensed data. In this way, a previous set of measured physiological characteristics or the trend derived from such characteristics may be recalculated based upon different calibration, equations, and/or other parameters. The recalculated characteristics and/or trend line may be subjected to additional analyses by the monitor 14 in research mode and/or may be visually reviewed by a caregiver.

In an embodiment, the operation of the monitor 14 and/or the performance of the staff at the facility over a time interval may be analyzed when in the research mode. For example, in such an embodiment, the number of alarms and/or the length of time alarms sound before being silenced may be analyzed in the research mode of the monitor 14. Such response time measurements may be used to evaluate staff performance and/or to evaluate whether the alarm limits for a particular patient are appropriate.

With the foregoing discussion in mind, one or more system settings or parameters of the monitor 14 may be evaluated based on the results of the analyses and recommendations made with regard to these setting or parameter values. For example, the monitor 14 may have various alarm limits set for a measured physiological characteristic and/or may apply certain calibration coefficients or algorithms in deriving such physiological characteristics. These parameters may initially be set to a default value) such as to a default value based on the patient's age, sex, physical condition, and so forth. After collection of physiological or monitor data over an interval of time and analysis of this collected data on the monitor in the research mode, suggested parameters (such as alarm limits, calibration coefficients, and/or algorithms) may be generated or selected based on the results of the statistical analyses (such as based on the number of apnea events, a calculated SPD index value, a recalculation of the $SpO_2$ values or trend line, and/or an analysis of the number of alarms and/or staff response time).

In an embodiment, the suggested parameters may be automatically implemented on the monitor 14. In another embodiment, the suggested parameters may be implemented on the monitor 14 when a user accepts the new parameters. For example, referring to FIG. 4, a message such as "Reconfigure Parameters" may be displayed on the display 20 along with respective yes/no soft key options such that a user can indicate whether or not the settings of the monitor 14 are to be reconfigured based on the analyses. In some embodiments the suggested settings may be displayed for review by the user, though in other embodiments the suggested settings are not displayed. After implementation of the new parameters, the monitor 14 may be returned to monitor mode, such as by selection of a suitably configured soft key 86, to continue monitoring the patient.

Figure 5:
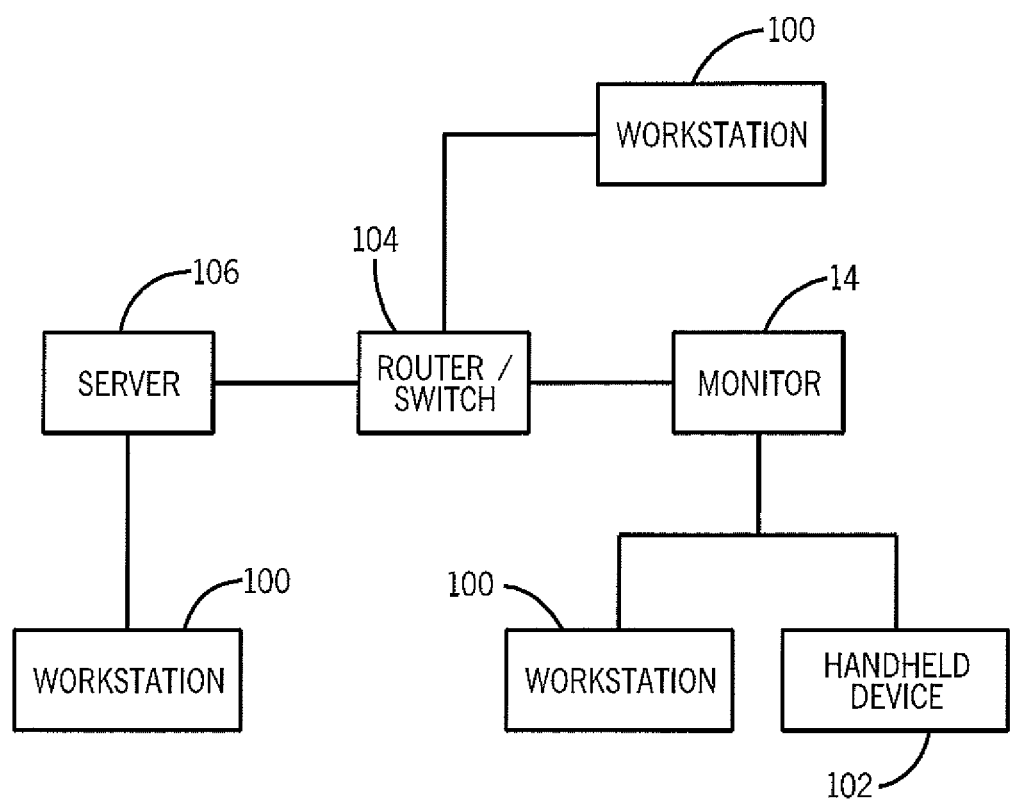
FIG. 5 is a block diagram of a data analysis system in accordance with embodiments.

In some embodiments the monitor 14 may communicate with other devices to facilitate or share the analyses performed using the implemented research mode. For example, referring to FIG. 5, the monitor 14 may be connected by wired or wireless techniques to a variety of systems such as one or more workstations 100 used in a clinical environment and/or to handheld devices 102 such as may be carried by doctors or other caregivers. As depicted, the workstations 100 and/or handheld device 102 may communicate with the monitor 14 by a variety of topologies. For example, a workstation 100 or handheld device 102 may communicate directly with the monitor 14 or may be connected via a router or switch 104 and/or server 106 provided as part of a network on which the monitor 14 resides. In such a networked embodiment, the monitor 14 may communicate with devices on a local network, such as within a department or hospital, or on attached or external networks.

In view of the various communication configurations in which the monitor 14 can participate, in certain embodiments, the research mode of the monitor 14 may also leverage these communication connections. For example, in one embodiment the monitor 14 may communicate in networked relationship (such as a peer-to-peer relationship) with a workstation or other processor-based system, such as a hand held device. In such an embodiment, the research mode application may be a networked application, taking advantage of computing and/or storage resources shared between the monitor 14 and the other peer-to-peer or networked devices. Thus, the research mode application may act as if it were implemented or running on a single platform even though aspects of the application may be stored and/or executed on the combination of networked devices. Further, in one such embodiment, resources such as input devices, i.e., keyboards, mice, and so forth, and display devices may be shared. In such an embodiment, an analysis may be configured or initiated at the monitor 14, workstation 100, and/or handheld device 102 using each devices respective input interface. Likewise, the results from the research mode analyses may be displayed on the connected device(s), such as at the workstation 100 or handheld device 102, as well as at the monitor 14. Thus, a caregiver may be located in their office or otherwise away from the monitor 14 and still perform data analyses on the monitor 14 using other available processor-based systems.

Similarly, in an embodiment the monitor 14 may host a web page that may be accessible by connected devices. The web page interface hosted on the monitor 14 in such an embodiment may allow a remote user to initiate, manipulate, and/or view results of a research mode analysis performed at the monitor 14. In such an embodiment, the research mode and corresponding analyses may be performed on the monitor 14, but the interface for controlling the analyses and viewing the results may reside on a device in communication with the monitor 14 which may be capable of interacting with the hosted web page. For example, a computer, personal digital assistant (PDA), or cell phone capable of displaying and interacting with a web page may be used to control and view the research mode processes executing on the monitor 14. In such an embodiment the device in communication with the monitor 14 may be equipped with a web browser to interact with the web page hosted on the monitor 14 but does not need any application specific software or hardware to implement the research mode analyses.

In addition, in some embodiments the research mode of the monitor 14 may function as a training or demonstration device. In such an embodiment, exemplary $SpO_2$ trend data for various disease states may be stored on the monitor 14 and displayed separately or in conjunction with acquired patient trend data. A user in the research mode might, therefore, be able to flip between an example of what a $SpO_2$ trend line looks like for one or more particular disease states and the $SpO_2$ trend line for a patient monitored by the monitor 14. Further, the user may be allowed to manipulate the configuration of the monitor 14 to see the effect of such manipulations of the displayed disease state trend data. In this manner, a user may familiarize himself or herself with how a disease state might be presented on the monitor 14 or how thresholds for caregiver alerts can be manipulated to trigger at the optimal time. This feature may be used in conjunction with a web page hosted on the monitor 14 to allow viewers at another location, such as a classroom, to compare the exemplary disease state trend lines with a tend line associated with a patient.

While only certain features have been illustrated and described herein, many modifications and changes will occur to those skilled in the all. It is, therefore, to be understood that the appended claims are intended to cover all such modifications and changes as fall within their true spirit.

What is claimed is:

1. A method for analyzing data, comprising:
   collecting data over a time interval using a physiological monitor in a monitoring mode;
   calculating one or more physiological characteristics of a patient over the time interval using one or more of a first coefficient, a first algorithm, or a first calibration; wherein the physiological monitor is configured to monitor the one or more physiological characteristics;
   entering a research mode on the physiological monitor concurrent with collecting data over the time interval, wherein the research mode is distinct from the monitoring mode of the physiological monitor; and
   analyzing the data on the physiological monitor in the research mode, wherein analyzing the data comprises recalculating the one or more physiological characteristics for the time interval using one or more of a second coefficient different from the first coefficient, a second algorithm different from the first algorithm, or a second calibration different than the first calibration.

2. The method of claim 1, comprising:
   adjusting one or more settings of the physiological monitor based on the results of the analysis.

3. The method of claim 1, comprising:
   adjusting one or more settings of the physiological monitor based on the results of the analysis; and
   collecting additional data using the physiological monitor.

4. The method of claim 1, comprising:
   displaying data indicative of one or more disease states on the physiological monitor when in the research mode; and
   comparing the collected data to the data indicative of one or more disease states.

5. The method of claim 1, wherein analyzing the data comprises performing at least one of a statistical analysis, a filtering operation, or a pattern recognition operation on the data.

6. The method of claim 1, wherein analyzing the data comprises accessing the physiological monitor via a networked processor-based system.

7. The method of claim 1, wherein analyzing the data comprises analyzing one or more measures related to monitor performance or staff performance during the time interval.

8. The method of claim 1, wherein the data corresponds to one or more of patient physiological data, sensor measurement values, or alarm response time measurements.

9. The method of claim 1, comprising automatically generating one or more recommended settings for the monitoring mode based on the recalculation of the one or more physiological characteristics.

10. A method for analyzing data, comprising:
    collecting data over a time interval using a physiological monitor in a monitoring mode;
    calculating at least one physiological characteristic or trend over the time interval by the physiological monitor in the monitoring mode;
    entering a research mode concurrently with the monitoring mode on the physiological monitor;
    accessing a set of data acquired in the monitoring mode by the physiological monitor over the time interval;
    executing one or more analysis routines on a processor of the physiological monitor in the research mode to analyze the set of data, wherein the processor executes the one or more analysis routines to recalculate the at least one physiological characteristic or trend over the time interval using the set of data;
    executing one or more statistical analysis routines on the processor of the physiological monitor to generate one or more recommended settings for the physiological monitor based on the results of the one or more analysis routines.

11. The method of claim 10, comprising:
    implementing the one or more recommended settings on the physiological monitor in response to a user input.

12. The method of claim 11, wherein the user input is received by the physiological monitor from a separate electronic device.

13. The method of claim 10, wherein the results of the one or more analysis routines are displayed.

14. The method of claim 10, wherein the set of data comprises one or more of patient physiological data, sensor measurement values, or alarm response time measurements.

15. The method of claim 10, comprising:
    displaying data indicative of one or more disease states on the physiological monitor; and
    comparing the set of data acquired in the monitoring mode by the physiological monitor over the time interval to the data indicative of the one or more disease states.

16. A physiological monitor comprising:
    a port capable of receiving sensor data;
    one or more memory or storage devices capable of at least storing the sensor data, one or more derived physiological characteristics, and/or one or more analysis routines; and
    one or more processors capable of processing the sensor data to derive the one or more physiological characteristics over a time interval of interest using a first algorithm or a first parameter when the physiological monitor is concurrently in a monitoring mode and a research mode, and wherein the one or more processors are capable of executing the one or more analysis routines to recalculate the one or more physiological characteristics over the time interval of interest when the physiological monitor is in the research mode concurrent with the monitoring mode, wherein the recalculation employs a second algorithm different from the first algorithm or a second parameter different than the first parameter.

17. The physiological monitor of claim 16, wherein the one or more memory or storage devices comprise at least one of a RAM, a ROM, or a mass storage device.

18. The physiological monitor of claim 16, wherein the one or more processors are also capable of executing one or more statistical analysis routines stored on the one or more memory or storage devices, wherein the statistical analysis routines generate one or more recommended settings for the physiological monitor based on the results of the analysis routines.

19. The physiological monitor of claim 16, wherein the one or more processors are capable of displaying one or more sets of sample data corresponding to respective disease states concurrently with at least one of the sensor data, the derived physiological characteristics, or the one or more analysis routines, and the analysis routines compare at least one of the sensor data or the derived physiological characteristics to the one or more sets of sample data corresponding to respective disease states.

20. A method for analyzing data, comprising:
collecting data over a time interval using a physiological monitor in a monitoring mode in which one or more physiological characteristics of a patient are calculated and monitored by the physiological monitor, wherein the one or more physiological characteristics are calculated based at least in part on a first set of one or more of coefficients, algorithms, or calibrations;
displaying the one or more physiological characteristics for the time interval on a display of the physiological monitor;
displaying one or more disease states on the display of the physiological monitor;
analyzing the data on the physiological monitor in a research mode concurrently with collecting data over the time interval, wherein analyzing the data comprises recalculating the one or more physiological characteristics for the time interval based at least in part on one or more different coefficients, algorithms, or calibrations, or any combination thereof and comparing the one or more physiological characteristics for the time interval to the one or more disease states;
generating one or more recommended settings for the physiological monitor based on the recalculated one or more physiological characteristics for the time interval; and
changing the first set to a second set of one or more coefficients, algorithms, or calibrations, wherein the second set is based at least in part on the one or more recommended settings.

21. The method of claim 20, comprising:
displaying data indicative of one or more disease states on the display of the physiological monitor;
wherein analyzing the data on the physiological monitor in the research mode concurrently with collecting data over the time interval comprises comparing the one or more physiological characteristics for the time interval to the one or more disease states.

* * * * *